United States Patent [19]
Reedy

[11] Patent Number: 5,903,344
[45] Date of Patent: May 11, 1999

[54] MATRIX ISOLATION APPARATUS FOR SPECTROSCOPIC ANALYSIS OF CHEMICAL COMPOUNDS

[75] Inventor: Gerald T. Reedy, Bourbonnais, Ill.

[73] Assignee: Reedy Scientific Instruments, Bourbonnais, Ill.

[21] Appl. No.: 08/807,959

[22] Filed: Feb. 28, 1997

Related U.S. Application Data

[63] Continuation-in-part of application No. 08/610,262, Mar. 4, 1996, abandoned.

[51] Int. Cl.$^6$ .................................................... G01N 21/01
[52] U.S. Cl. ............................................................ 356/244
[58] Field of Search ............................... 356/36, 38, 244; 250/338 R, 341, 304, 352, 443.1, 288 A; 422/89; 464/7, 17, 24

[56] References Cited

U.S. PATENT DOCUMENTS

| | | | |
|---|---|---|---|
| 3,853,590 | 12/1974 | Kadison et al. | 117/47 |
| 4,158,772 | 6/1979 | Reedy | 250/338 |
| 4,473,295 | 9/1984 | Doyle | 356/244 |
| 4,549,807 | 10/1985 | Hoffmaster | 356/318 |
| 4,594,226 | 6/1986 | Reedy | 422/89 |
| 4,688,936 | 8/1987 | Reedy | 356/36 |
| 4,812,041 | 3/1989 | Doyle | 356/346 |
| 4,848,914 | 7/1989 | Shiraishi | 356/440 |
| 5,538,643 | 7/1996 | Kallos et al. | 210/656 |

*Primary Examiner*—Frank G. Font
*Assistant Examiner*—Michael P. Stafira
*Attorney, Agent, or Firm*—Greer, Burns & Crain Ltd.

[57] ABSTRACT

Apparatus for spectroscopic analysis of chemical compounds in samples released from a gas chromatograph is configured for placing the samples in matrix isolation for exposure to a beam of light generated from a spectrometer. The apparatus includes a vacuum chamber, housing a generally cylindrical, axially rotating sample disk having an axle and a mirrored surface, which is provided for receiving the samples from the gas chromatograph. A support block supports the rotating disk within the vacuum chamber. Also included in the apparatus is a cooling device which is in contact with the support block for cryogenically cooling the mirrored surface. Further, the disk is configured such that it rotates relative to the stationary cooling device. Also featured is a sample deposition apparatus which displaces a sample deposition nozzle to avoid contamination of the mirrored surface, and positions the deposition nozzle relative to the sample disk to obtain real time sample analysis.

35 Claims, 9 Drawing Sheets

MATRIX ISOLATION APPARATUS FOR SPECTROSCOPIC ANALYSIS OF CHEMICAL COMPOUNDS

RELATED APPLICATION

This is a Continuation-In-Part of U.S. patent application Ser. No. 08/610,262 filed Mar. 4, 1996, now abandoned for A COLLECTOR DEVICE FOR USE IN SPECTRAL ANALYSIS.

BACKGROUND OF THE INVENTION

The present invention relates generally to a method and apparatus for spectroscopic analysis of chemical compounds that have been separated by a gas chromatograph and suspended in a frozen matrix isolated state, and specifically to an arrangement for collecting, entrapping and displaying the separated compounds in a state of matrix isolation for spectroscopic analysis.

Conventionally, gas chromatographs been widely used in conjunction with various spectroscopic instruments, for example, mass spectrometers, for analysis of chemical compounds. In such systems, gas chromatographs, which are known instruments for separating mixtures of chemical compounds, separate the samples into their respective individual compounds. The separated compounds are then analyzed by the mass spectrometers to determine the identity of each compound.

While conventional mass spectrometers may be sufficient for supplying approximate analyses of the separated compounds, they are inadequate for distinguishing between compounds having molecules that are very similar, i.e., isomers. The problem is compounded when the quantity of a sample being analyzed is small. In addition, the mass spectrometer does not offer any means for preserving the samples for further analysis at a later time. For these reasons, the conventional gas chromatograph/mass spectrometer system is unsuited for identification of minute amounts of compounds requiring a high degree of specificity, such as when exact isomer identification is required.

To address the above-described shortcomings of the gas chromatograph/mass spectrometer system, a matrix isolation infrared spectroscopic technique has been developed to be used in conjunction with the gas chromatograph. In this system, a chemical sample is gas chromatographically separated, and mixed with an inert substance, such as argon or krypton gas. Both the sample and the inert gas are then deposited onto a smooth mirrored surface that is cryogenically cooled to about 10° to 20° K, which results in the molecules of each compound being entrapped within a frozen matrix of solidified inert gas. The infrared spectrum of each molecule is then measured for high resolution identification of each compound in the sample. In this manner, an accurate analysis of the chemical compounds is achieved with more certainty than from conventional mass spectrometers, particularly when it is important to distinguish among compounds that have very similar molecules and when small quantities of samples are being tested. An added advantage of this technique is that it permits retention of the sample in a suspended state over an extended period of time to allow a confirming analysis at a later time.

A known apparatus for incorporating the matrix isolation technique with a gas chromatograph is disclosed in U.S. Pat. No. 4,688,936 to the present inventor, which is incorporated by reference herein. That apparatus includes a sample collection vacuum chamber. Provided within the vacuum chamber is a specular carousel having a polished surface, upon which the gas sample from the gas chromatograph is deposited by a delivery nozzle. The specular carousel is configured to rotate in a helical pattern so that there is a continuous surface for the sample to be deposited. Coupled to the vacuum chamber is a vacuum pump for creating a high vacuum. The expander module of a closed cycle refrigerator, which is also coupled to the vacuum chamber, is included for supporting and cryogenically cooling the specular carousel. When a beam of infrared (IR) light enters the vacuum chamber, it is adjustably directed onto the sample deposited on the carousel surface by a first mirror. A second mirror, positioned adjacent to the first mirror, receives the IR beam reflected from the carousel surface and aims the IR beam to an infrared light detector.

One disadvantage of the system disclosed in U.S. Pat. No. 4,688,936 is that the specular carousel is bolted to the expander module and its rotation is derived by rotating the entire expander module. This is an inefficient method of rotating the specular carousel, because the only function of the expander module is to cool the specular carousel, and therefore, configuring the expander module to also rotate the carousel unnecessarily complicates the cooling system and its manufacture. Moreover, the rotation of the carousel via the expander module, rather than rotating it independently, requires a much larger scale of motion, because the motion is transferred to a number of different components before actually reaching the carousel. Consequently, a precise rotation of the carousel is not achieved, and the sample is not deposited in a consistent helical pattern to be exposed by the IR beam.

A sample block that rotates independently of a cooling expander is disclosed in U.S. Pat. No. 4,158,772 to the present inventor. However, it has been found that the arrangement disclosed in that patent results in poor heat transfer between the cooling expander and the sample block. This is because the heat transfer is conducted through threads on which the sample block rotates and translates, resulting in limited contact between the sample block and the threads. In addition, the sample block of this patent is octagonally shaped, which reduces the availability of the sample collecting surfaces.

Another disadvantage of the above-identified prior art matrix isolation analysis systems is that the point of sample deposition on the carousel is 180 degrees away from the point where spectroscopic analysis is conducted. As a result, the recording of the IR beam for analysis is a "post-run" operation, in contradistinction to a "real time" operation. This drawback results in unwanted delay in the analysis.

Still another disadvantage of the prior art matrix isolation analysis systems is that the delivery nozzle is stationary, which results in unwanted excess sample being deposited on the sample block due to weeping. Another disadvantage of the systems having the stationary delivery nozzle is that unwanted solvent from the sample is discharged onto the sample block, i.e., an upstream valving operation for eliminating the solvent must be performed on the sample block. A displaceable delivery nozzle is disclosed in U.S. Pat. No. 4,594,226 to the present inventor. However that delivery nozzle is not displaceable in a manner which would prevent unwanted excess sample from contaminating the carousel surface.

Yet another disadvantage of the prior art matrix isolation analysis system is that the first and the second mirrors are two separate pieces, and require adjustments relative to each other. In addition, the adjustment assembly on which the two mirrors are mounted for adjusting the two mirrors relative to the carousel surface only allows two dimensional adjustments.

Thus, it is a first object of the present invention to provide an apparatus for spectroscopic analysis of chemical compounds having a deposition surface that moves independently of the cryogenic cooling system, yet provides efficient heat transfer between the deposition surface and the cooling system.

Another object of the present invention is to provide an apparatus for spectroscopic analysis of chemical compounds having a sample deposition point at close proximity to the point of spectroscopic analysis to enable "real time" examination of the sample.

Yet another object of the present invention is to provide an apparatus for spectroscopic analysis of chemical compounds having a sample delivery nozzle that can be rapidly displaced from the deposition surface to prevent excess sample and unwanted solvent component of the sample from contaminating the deposition surface.

Still another object of the present invention is to provide an apparatus for spectroscopic analysis of chemical compounds wherein the two mirrors for focusing and redirecting the IR beam are fabricated in a single block, and an adjustment assembly for adjusting the mirrors relative to deposition surface allows for three dimensional adjustments.

BRIEF SUMMARY OF THE INVENTION

The above-identified objects are met or exceeded by the present apparatus for spectroscopic analysis of chemical compounds in complex gas chromatographic samples. The apparatus is configured for placing the samples in matrix isolation for exposure to a beam of light generated from a spectrometer. It includes a vacuum chamber having an inlet window for allowing the beam of light to enter the vacuum chamber. A generally cylindrical, axially rotating sample disk is housed within the vacuum chamber and has an axle and a mirrored surface which is provided for receiving the samples from the gas chromatograph. A support block supports the rotating disk within the vacuum chamber. The present apparatus also features a cooling device which is in contact with the support block for cryogenically cooling the mirrored surface. Further, the rotating mirrored sample disk is configured such that it rotates relative to the cooling device, which is stationary.

Another feature of the present system is that the sample is exposed to the beam of light via a mirror assembly, which has a control mechanism for allowing the mirror assembly to be adjusted in the X, Y and Z directions. This mirror assembly focuses the beam entering through the inlet window onto an examination point on the mirrored surface for penetration through the samples, and projects the beam reflected from the examination point out through the outlet window for detection by an externally mounted beam detector.

A transfer tube, disposed at least partially in the vacuum chamber, has a delivery nozzle for depositing the samples onto the mirrored surface. Still another feature of the present system is that connected to the delivery nozzle is a displacing mechanism for pivotally and transversely displacing the delivery nozzle between a deposit position and a rest position. Yet another feature of the present system is that to enable real time examination of the samples, the samples are deposited on the mirrored surface at a close proximity to, and upstream of, the examination point.

DETAILED DESCRIPTION OF THE INVENTION

Figure 1:
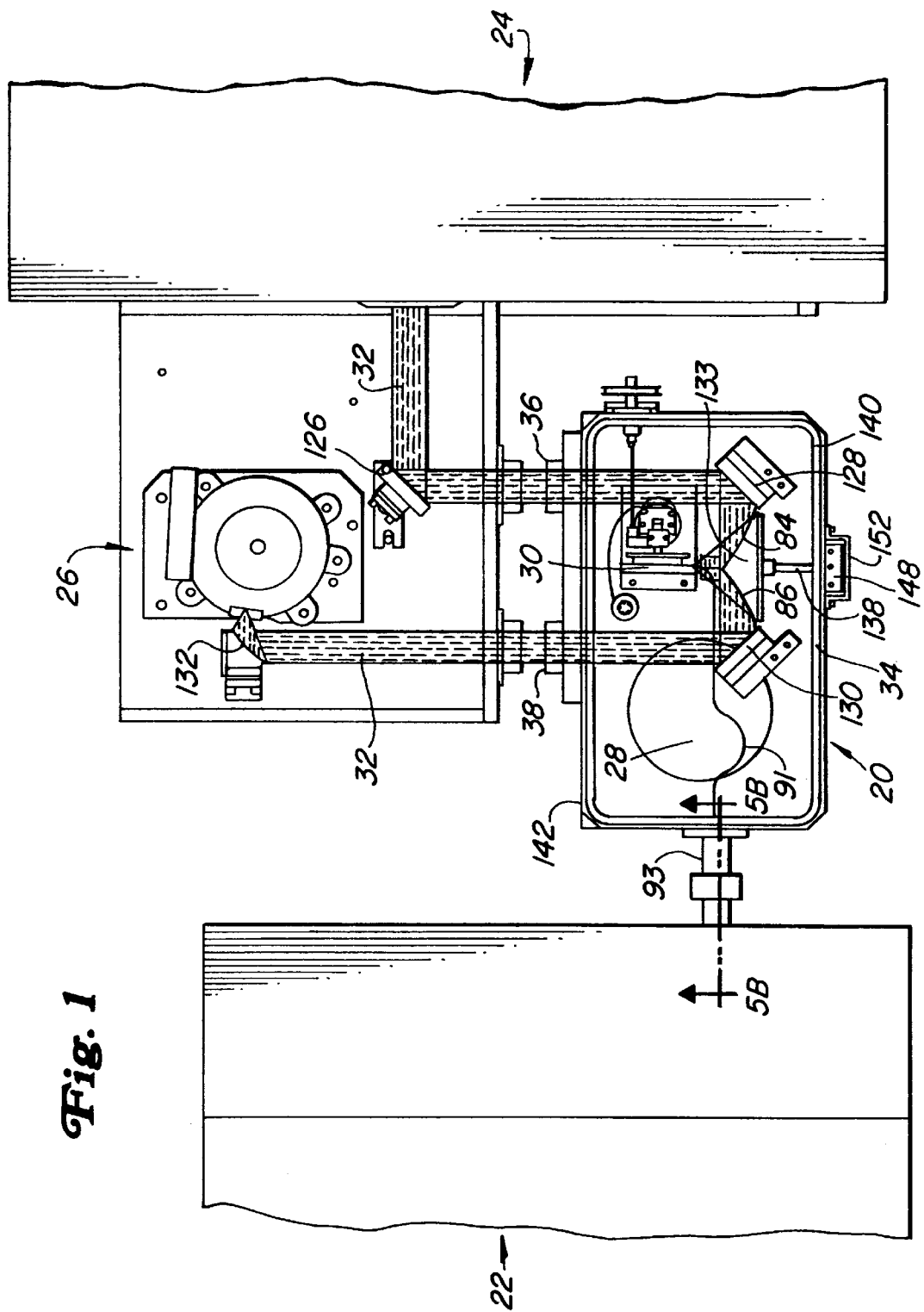
FIG. 1 is a diagrammatic overhead plan view of the apparatus for spectroscopic analysis of chemical compounds embodying the present sample analysis system.

Referring now to FIG. 1, a matrix isolation (MI) unit, generally designated 20, is shown with a gas chromatograph, an infrared (IR) spectrometer and an infrared (IR) detector, generally designated 22, 24 and 26, respectively. FIG. 1 depicts the overall major components of the present analysis system and the manner in which they are connected. The gas chromatograph 22, preferably of the type supplied by Hewlett-Packard as Model 6890 GC, or equivalent, is coupled to a mixture source (not shown) which provides a carrier gas such as helium and a matrix gas such as argon. In the preferred embodiment, the helium-to-argon ratio is approximately 99 percent helium and 1 percent argon. A sample of chemical compounds to be analyzed is typically in a liquid solution, and is injected into the carrier gas stream by use of a hypodermic syringe (not shown) or other commonly known means of introducing sample material into a gas chromatograph. Once in the gas chromatograph 22, the sample vaporizes rapidly into the carrier gas stream. The carrier gas transports the sample through the gas chromatograph 22 where the sample is separated into its constituent compounds according to the well established principles of gas chromatography.

Entrained within the carrier gas, the separated compounds exit the gas chromatograph 22 and flow via a pressure gradient into the MI unit 20, which will be more comprehensively described below. In the MI unit 20, the carrier gas, including the sample and the matrix gas, is deposited onto a cryogenically cooled rotating mirrored surface 30 (best seen in FIG. 4). On the mirrored surface 30, the argon condenses and "traps" or "isolates" the sample molecules from one another in a "matrix" of solid argon. The helium gas, however, is pumped out of the MI unit 20 by a vacuum pump 28 because it is noncondensable and of low molecular weight. As a result, a sequence of separated sample compounds is collected along a track of solid argon approximately 0.012 inch wide and having a ratio of argon molecules to sample molecules at a given spot of approximately 1000 to 1.

The analysis of the sample occurs as the mirror surface 30 rotates and exposes the compounds to a beam of infrared (IR) light 32 generated by the IR spectrometer 24 of a Fourier transform type, a suitable model being the Nicolet Magna 550 spectrometer manufactured by Nicolet Instrument Corporation of Madison, Wis. After the IR beam 32, which is approximately 0.012 inch in width to correspond to the width of the track of solid argon and sample compounds, penetrates the frozen matrix, it is reflected to the IR detector 26, which is preferably of the type having an IR detector element cooled by a supply of liquid nitrogen. Analysis of the IR beam 32 is conducted by a computer (not shown) based on IR spectra which reveal details about the vibration of the molecules, and hence, their exact identity.

The MI unit 20 includes a vacuum chamber 34, which has an inlet window 36 for allowing the IR beam 32 to enter the vacuum chamber, and an outlet window 38 for allowing the IR beam 32 to exit the vacuum chamber. The windows 36, 38 are made of polished, infrared-transparent salt plates which are sealed against the walls of the chamber 34. A vacuum is created inside the vacuum chamber 34 via the vacuum pump 28, which is coupled to the vacuum chamber 34 at the bottom 35 thereof (best seen in FIG. 5A). The vacuum pump 28 should be of a high vacuum type such as a turbomolecular pump that is capable of producing vacuum at $10^{-5}$ Torr or better inside the vacuum chamber.

Figure 2:
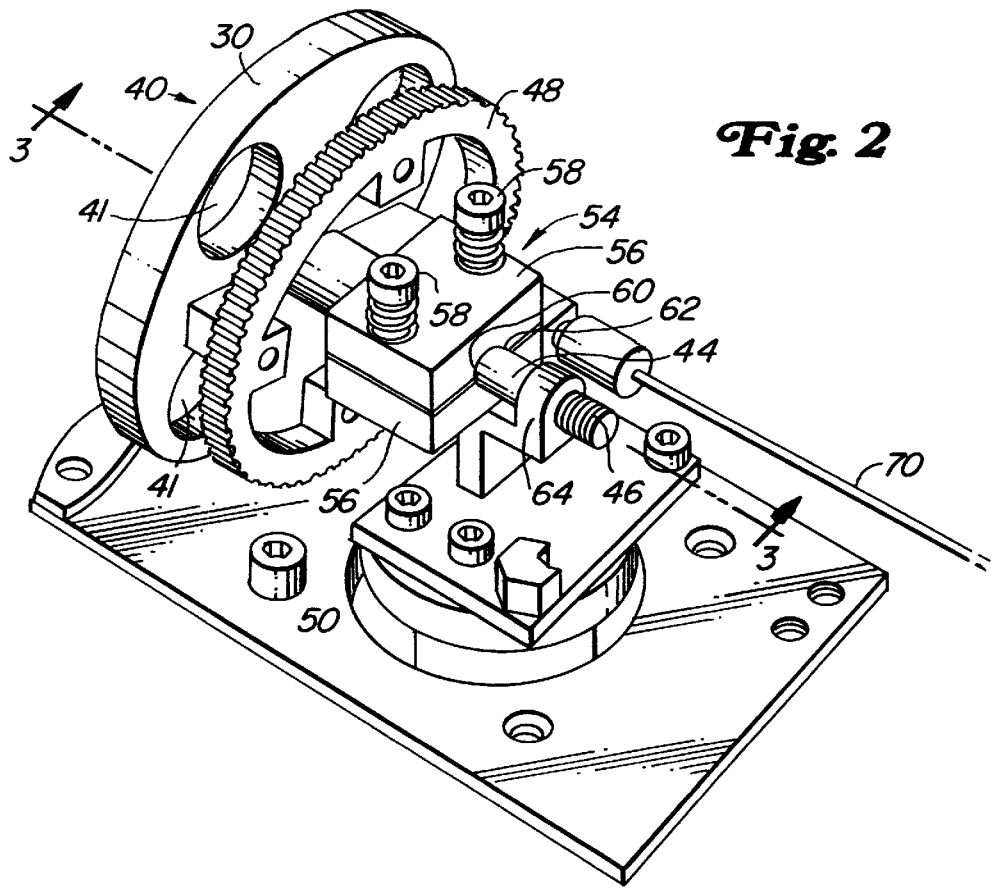
FIG. 2 is a top perspective view of a sample disk and a support mount that is a part of the present system.
Figure 3:
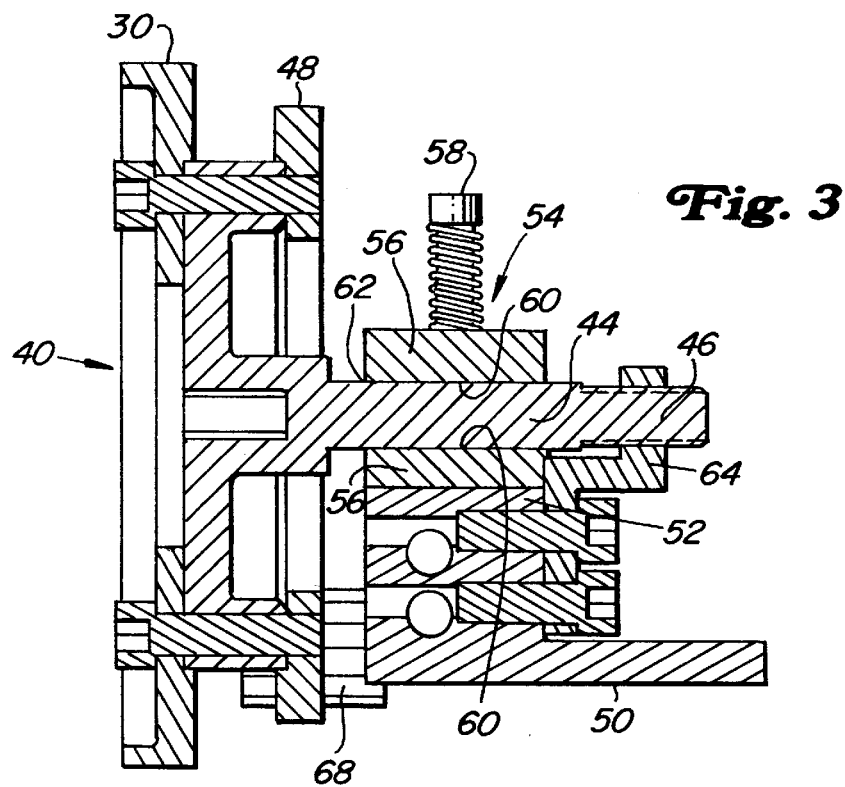
FIG. 3 is a sectional view of the sample disk and the support mount taken along the line 3—3 of FIG. 2 and in the direction generally indicated.
Figure 4:
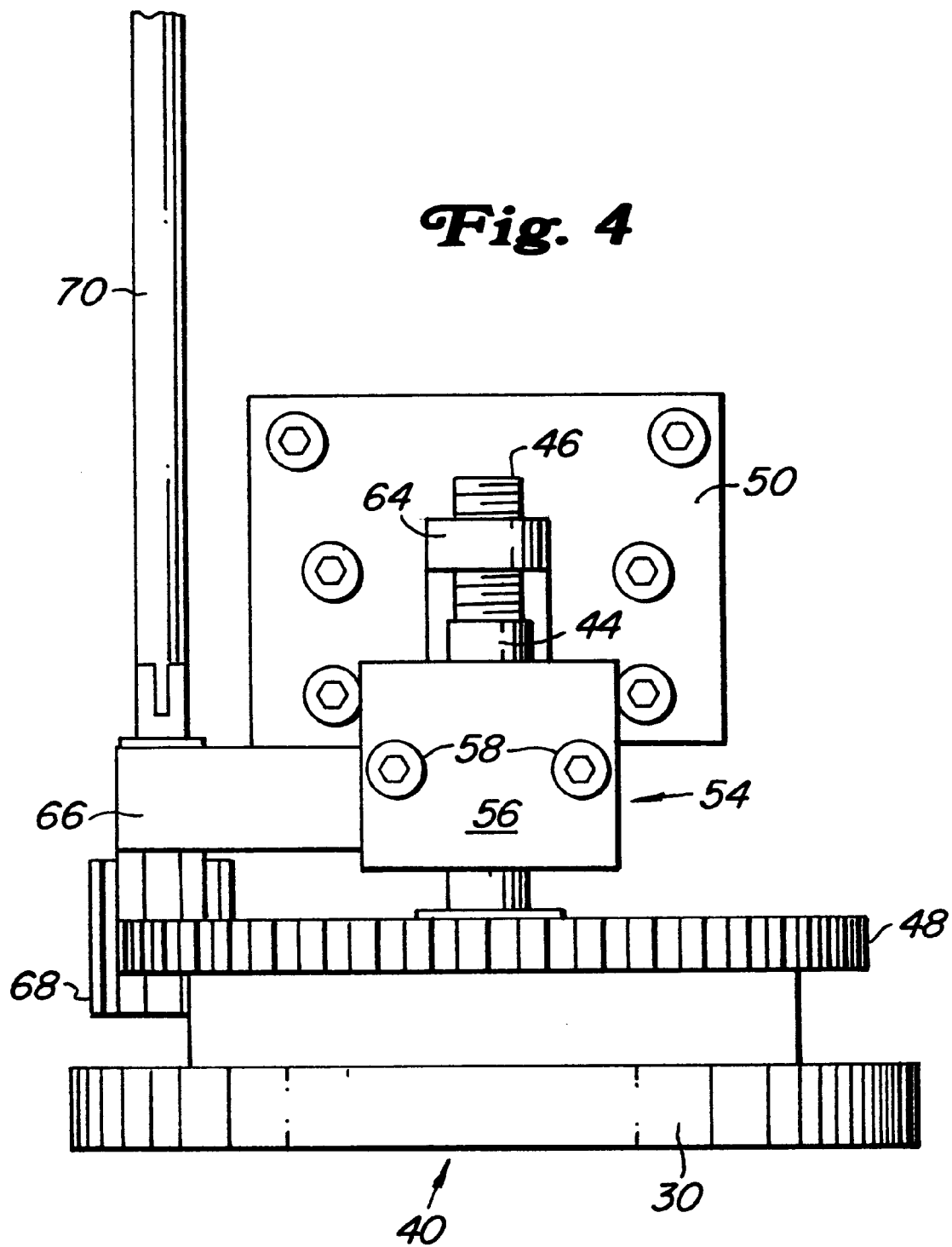
FIG. 4 is a top view of the sample disk and the support mount shown in FIGS. 2 and 3.

Referring now to FIGS. 2–4, the MI unit 20 further includes a generally cylindrical, axially rotating sample disk located in the vacuum chamber 34, and generally designated 40. The sample disk 40 includes the mirrored surface 30, which is configured for receiving the sample of chemical compounds from the gas chromatograph 22. A temperature of approximately 10° K is maintained on the mirrored surface 30 so that the sample discharged from a delivery nozzle 42 (best seen in FIG. 6) in a gaseous state instantly freezes on the mirrored surface 30 as it comes in contact therewith, resulting in the molecules of each chemical compound being entrapped in solid argon. In the preferred embodiment, the sample disk 40 has four circular holes 41 evenly spaced apart (best seen in FIG. 2). This reduces the mass of the sample disk 40, and decreases the time that is required to bring the mirrored surface 30 to the preferred cryogenic temperature.

Extending from the sample disk 40 is an axle 44, which has a threaded tip region 46 at the opposite end from the mirrored surface 30. A spur gear 48 is concentrically fastened to the sample disk 40 and is axially offset from the disk towards the threaded region 46. The sample disk 40 and the spur gear 48 are supported in the vacuum chamber 34 by a support mount 50. Attached to a top 52 of the support mount 50 (best seen in FIG. 3) is a spring loaded split bearing, generally designated 54, which includes a pair of plates 56 pressed together by a pair of spring loaded screws 58. Formed into each plate 56 is a half cylindrical passage 60, which defines a whole cylindrical passage 62 (best seen in FIG. 3) when the two plates 56 are pressed together. The split bearing 54 holds the axle 44 in the cylindrical passage 62 such that the axle 44 is permitted to move in translational and axially rotational directions. In the preferred embodiment, the plates 56 are made of silver to provide lubricity in place of conventional lubricating agents such as grease or oil, which at cryogenic temperatures have a tendency to lose their lubricating properties.

Concentric with the cylindrical passage 62 and bolted to the support mount 50 is a thrust nut 64, which threadably engages the threaded tip region 46 of the axle 44. A pinion restraint 66 is also attached to the support mount 50 (best seen in FIG. 4) for rotatably holding a pinion gear 68 (best seen in FIG. 4). The pinion gear 68 engages the spur gear 48, and is driven, via a pinion drive shaft 70, by a stepping motor (not shown) external to the vacuum chamber 34. Ah important feature of the pinion gear 68 is that it is long enough to accommodate translational movement of the disk 40, the axle 44 and the spur gear 48.

In operation, the stepping motor (not shown) rotates the pinion gear 68, which in turn rotates the spur gear 48, and thereby initiates the axial rotation of the sample disk 40. As the spur gear 48 rotates, the threaded tip region 46 of the axle 44, which is engaged with the thrust nut 64, causes the sample disk 40 to also be displaced in the translational direction along the central axis of the axle 44. In this manner, the sample disk 40 is constructed and arranged to rotate in a helical pattern, thus resulting in the sample being deposited on the mirrored surface 30 in a likewise helical pattern. In the preferred embodiment, the width of the mirrored surface 30 is sufficient to accommodate five helical tracks, each of which is approximately 0.012 inch wide and being spaced apart approximately 0.030 inch. A computer (not shown) is operatively connected to the stepping motor for controlling the axial rotation of the sample disk 40.

Figure 5A:
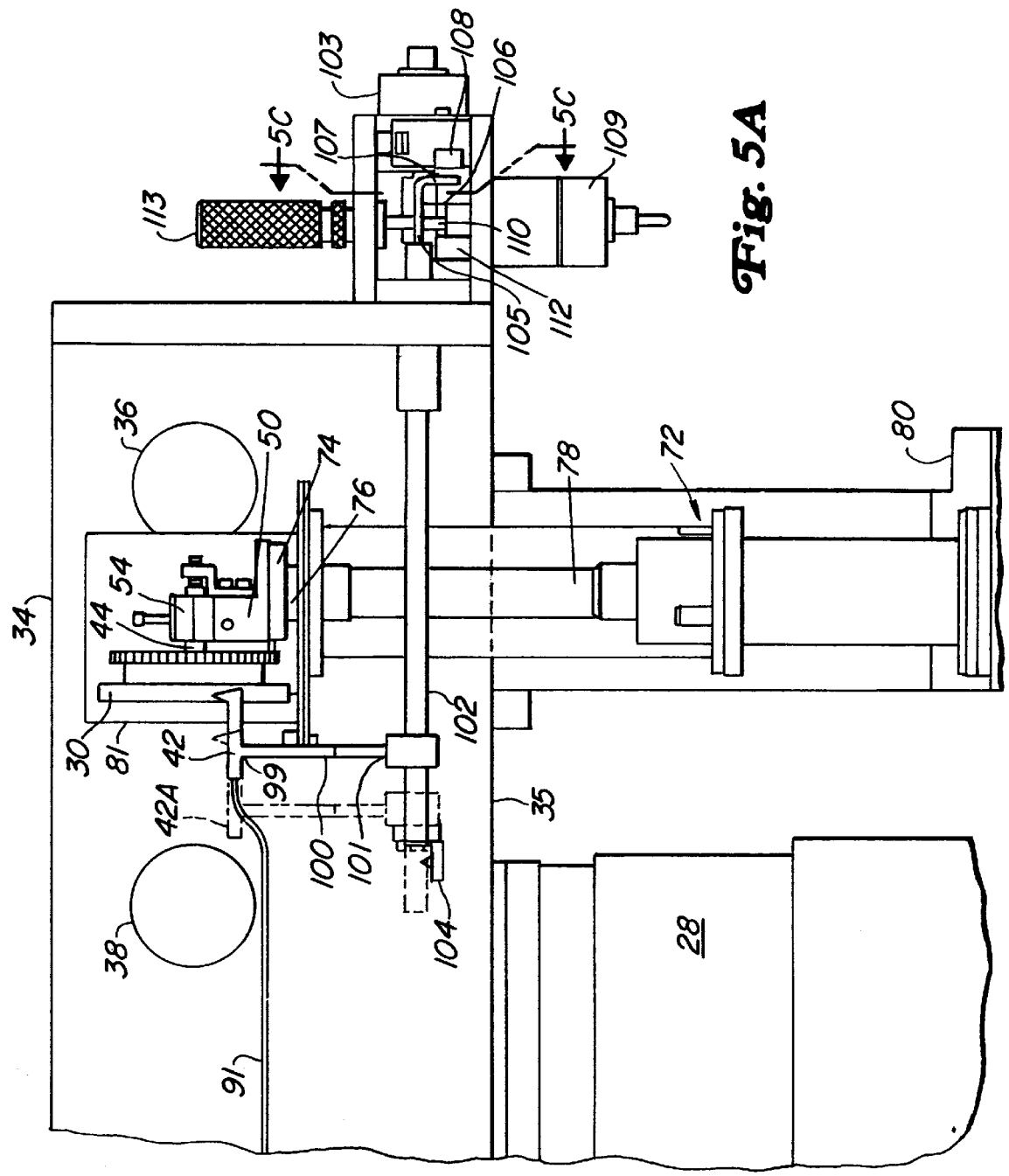
FIG. 5A is a diagrammatic partial front elevational view of the apparatus of FIG. 1.

Referring now to FIG. 5A, a view of the MI unit 20 is illustrated so that a cryogenic cooling device is shown, and generally designated 72. The cooling device 72, which, in the preferred embodiment is a Coolstar closed cycle helium refrigeration system manufactured by Edwards High Vacuum of Crawley, England, is coupled to and extends into the vacuum chamber 34. A cold head 74 is attached to a distal end 76 of a stationary piston 78 that extends from a base 80 of the cooling device 72. In the preferred embodiment, the temperature at the cold head 74 is approximately 10° K. The cold head 74 serves as a platform upon which the support mount 50 is connected, and also as the heat transfer interface for cooling the mirrored surface 30 to the desired cryogenic temperature. Heat transfer occurs from the cold head 74 to the mirrored surface 30 through a path including the support mount 50, the split bearing 54, the axle 44 and the sample disk 40, resulting in the temperature of the mirrored surface 30 being equal to the cold head 74. To improve heat transfer, an indium gasket (not shown) is provided between the cold head 74 and the support mount 50 and between the sample disk 40 and the axle 44. Additionally, the split bearing 54 is silver soldered onto the support mount 50, which also increases head transfer. Further, the support mount 50, the axle 44 and the sample disk 40 are made of copper, the properties of which are well suited for heat transfer at cryogenic temperatures.

Once assembled, the sample disk 40, the non-bearing surfaces of the split bearing 54 and the support mount 50 are coated with a layer of gold to protect the polished copper surfaces from tarnishing and to reflect radiant heat. In addition, they are also covered with a heat shield 81 which entirely encases these components, exclusive of the area on the mirrored surface 30 where the sample is deposited and upon which the IR beam 32 is incident. The heat shield 81 serves to protect the enclosed components from the relatively higher temperature inside the vacuum chamber 34.

Figure 6:
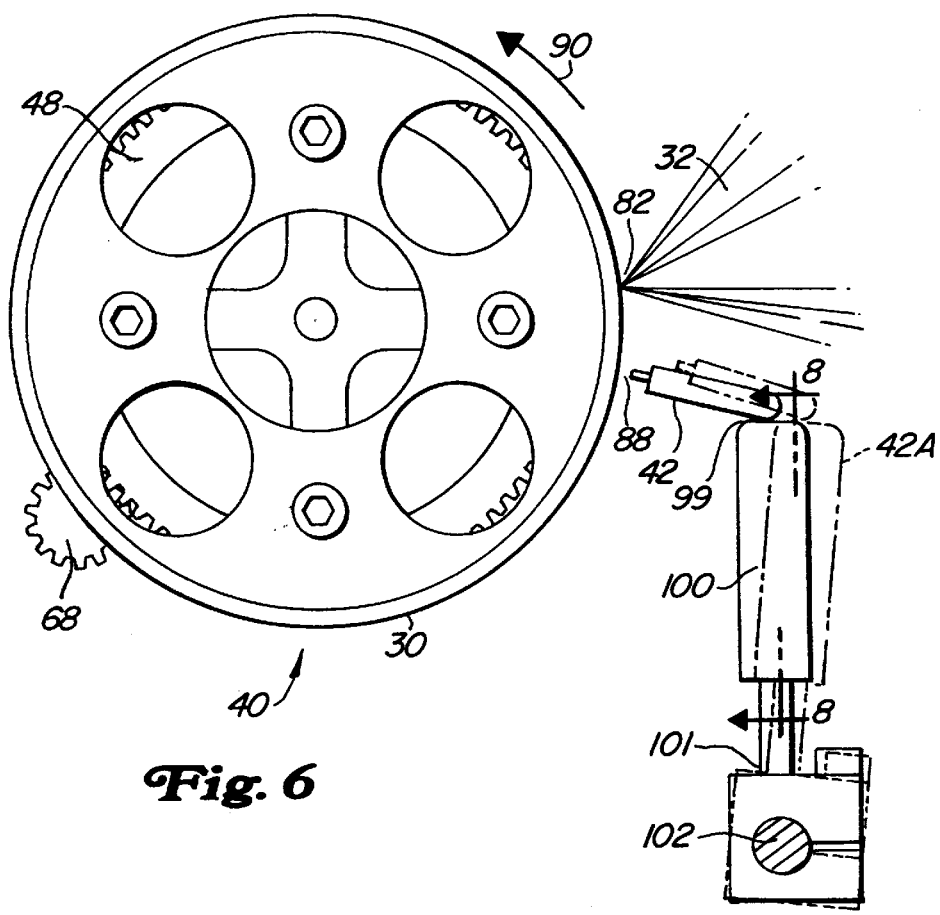
FIG. 6 is an end view of the sample disk showing the position of an incident light beam relative to the point of sample deposition.

Referring now to FIG. 6, the sample disk 40 is shown illustrating the position of the IR beam 32 incident thereon relative to the position where the sample of chemical compounds is deposited. According to an important aspect of the present invention, the IR beam 32 from the IR spectrometer 24 (best seen in FIG. 1) is incident upon an examination point 82 by a pair of objective mirrors 84, 86 (best seen in FIG. 9), which will be described in more detail below. The sample is deposited onto a deposition point 88 by the delivery nozzle 42 in close proximity and upstream of the examination point 82, as determined by the rotational direction of the sample disk 40. In the preferred embodiment, the deposition point 88 and the examination point 82 are approximately 15° apart, and the rotation of the sample disk 40 is indicated by a rotation arrow 90.

In the present invention, it is possible to place the examination point 82 and the deposition point 88 in close proximity to each other because the plane of incidence and reflection of the IR beam 32 is perpendicular to the line of rotation of the sample disk 40. In the prior art inventions described above, the deposition point is on the same plane as the examination point, and it is not possible to closely space these points together because of structural limitations of placing the objective mirrors adjacent to the delivery nozzle. The deposition and examination point arrangement of the present invention allows a user to analyze the sample in "real time," i.e., in about 1 minute from the moment the sample is deposited onto the deposition point 88, rather than waiting for the sample to reach the examination point 82 that is 90° away, as in the prior art invention disclosed in the U.S. Pat. No. 4,688,936 or 180° away as in the U.S. Pat. Nos. 4,158,772 and 4,594,226. This is a significant advantage, because at the speed that would allow each compound to collect in a compact circular area appropriate for examination by the infrared beam, it would take about 15 minutes for the sample disk 40 to make a 90° turn.

Referring back to FIGS. 5A, 5B, 7A and 7B, the delivery nozzle 42 for depositing the sample onto the mirrored surface 30 is shown connected to a flexible transfer tube 91. The transfer tube 91, which has an outer diameter of approximately 0.035 inch, leads directly into the gas chromatograph 22, and supplies the sample in the gaseous state to the delivery nozzle 42 to be discharged therefrom. To maintain the sample in the gaseous state, the transfer tube 91, which is made of stainless steel, is heated to a temperature of about 250° to 300° C. by applying an electric current of approximately 1.2A along its length. In the preferred embodiment, the transfer tube 91 is also furnished with an internal tube 92 having an outer diameter of approximately 0.009 inch and made of either fused silica or stainless steel with a silica lining (best seen in FIG. 7B), which provides an inert surface for assisting with the transfer of the sample through the transfer tube 91 without decomposition.

Figure 5B:
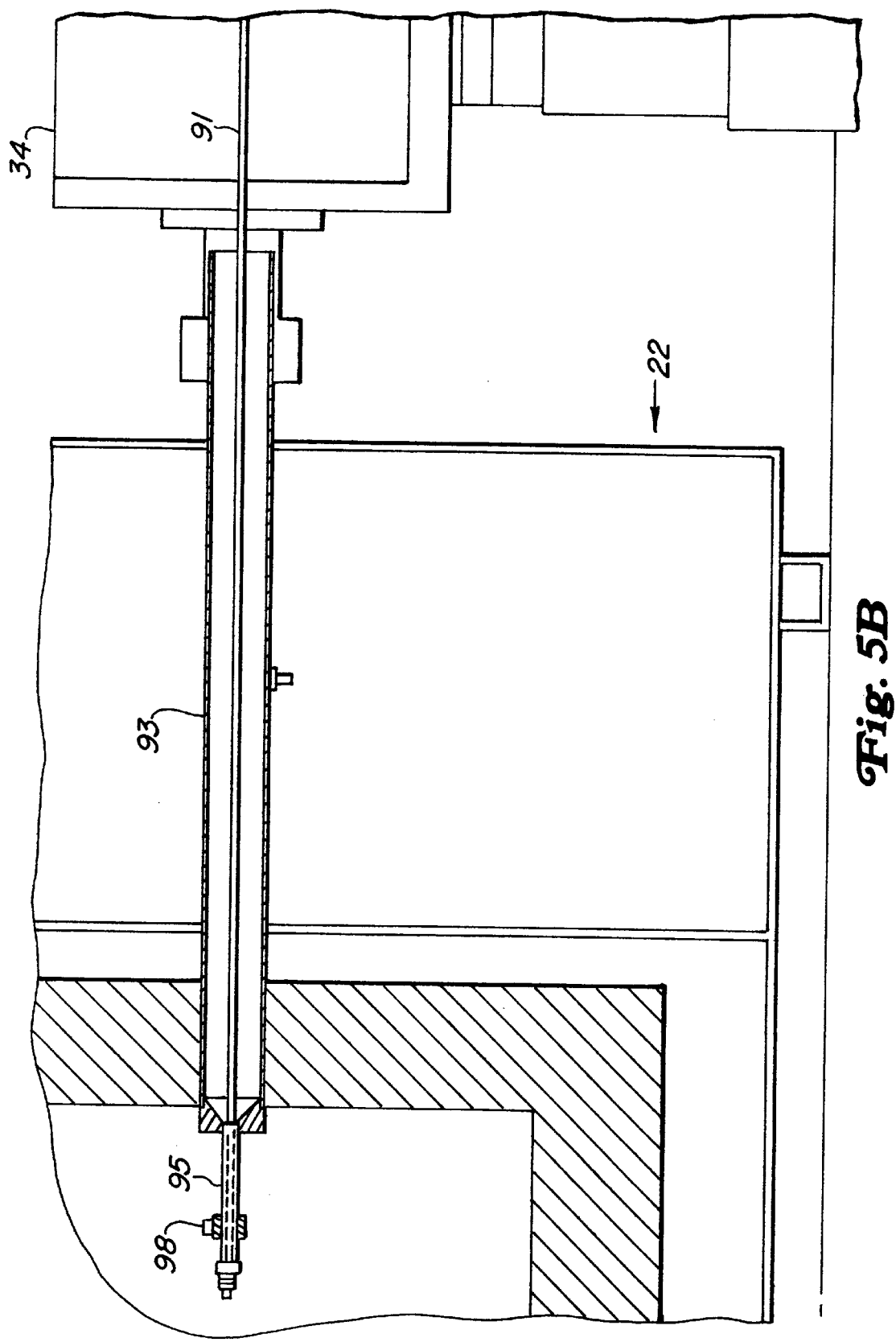
FIG. 5B is a diagrammatic, enlarged section taken along the line 5B—5B of FIG. 1 and in the direction generally indicated.
Figure 7A:
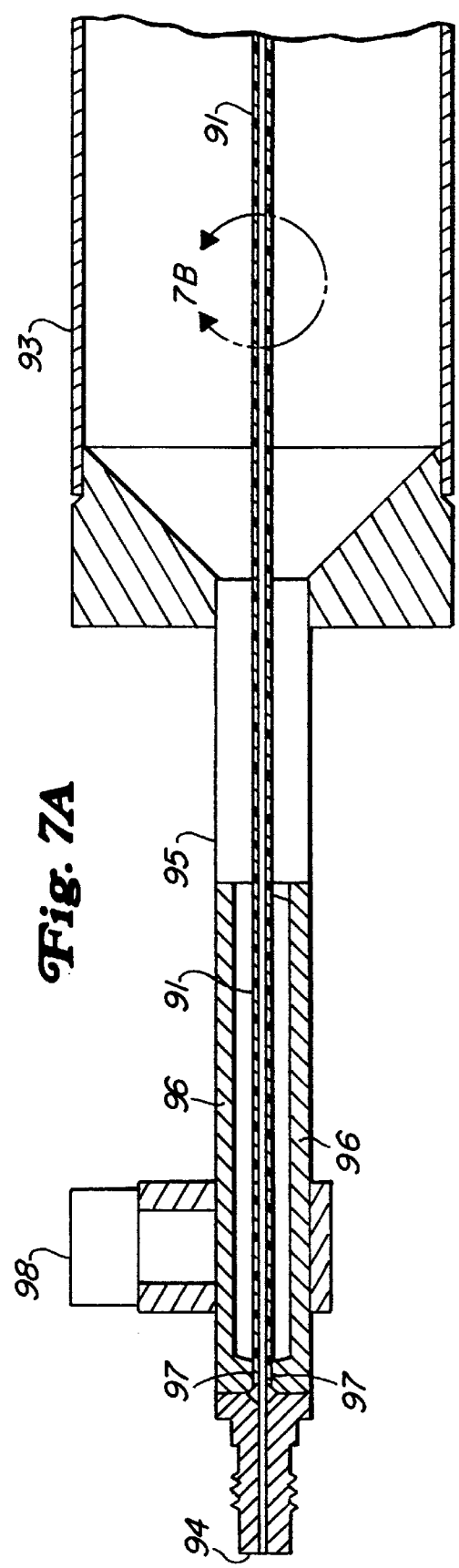
FIG. 7A is a vertical sectional enlargement of a portion of FIG. 5B.
Figure 7B:
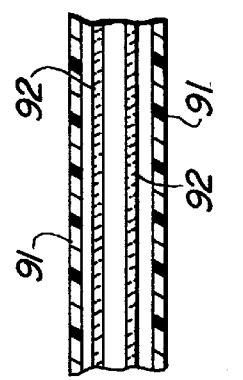
FIG. 7B is vertical sectional enlargement of a portion of FIG. 7A.

Upon exiting the vacuum chamber 34, the transfer tube 91 is coaxially encased within a vacuum extension tube 93 (best seen in FIGS. 5B and 7A). The extension tube 93 is coupled between the vacuum chamber 34 and the gas chromatograph 22. It is also in fluid communication with the vacuum chamber 34, and is sealed from the environment at the opposite end inside the gas chromatograph 22 by a vacuum seal (not shown) at the distal end 94 of the neck portion 95 of the extension tube 93. This arrangement allows the vacuum to extend into the extension tube 93, thus insulating the heated transfer tube 91 from the colder ambient air. The transfer tube 91 is held in the coaxial relationship with the extension tube 93 by a bracket (not shown) at the end coupled to the vacuum chamber 34 and by a tube sleeve 96 at the end coupled to the gas chromatograph 22. Inserted into the tube sleeve 96, the transfer tube 91 is welded at its front tip 97 to the tube sleeve. Assembled in this manner, the sleeve 96 and the transfer tube 91 are inserted into the neck portion 95 of the extension tube 93 and held in place by a tube clamp 98, which tightens around the neck portion 95 to compress the tube sleeve 96 and the neck portion together. The tube clamp 98 additionally serves as a terminal for supplying the electric current to the transfer tube 91 for heating purposes, the path of current flow being from the clamp 98 to the neck portion 95, to the tube sleeve 96 and to the transfer tube 91 via the front tip 97.

Figure 5C:
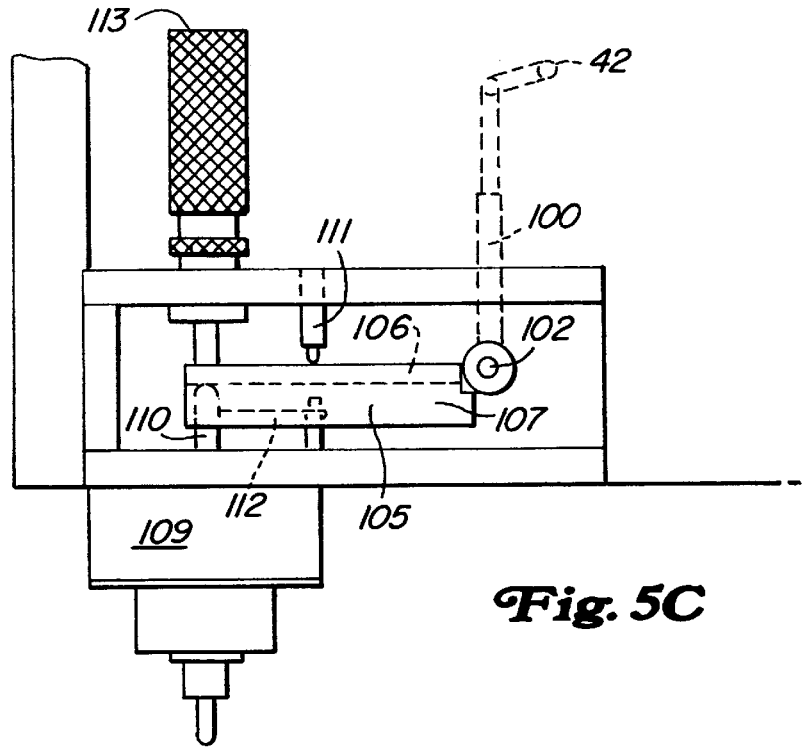
FIG. 5C is a diagrammatic, enlarged section taken along the line 5C—5C of FIG. 5A and in the direction generally indicated.

Referring now to FIGS. 5A, 5C and 6, in accordance with an important aspect of the present invention, the delivery nozzle 42 is connected to the top end 99 of a post 100 (best seen in FIG. 6), which at its bottom end 101 is connected to a nozzle shaft 102. Extending outside the vacuum chamber 34, the nozzle shaft 102 is threadably received by a stepping motor 103 (best seen in FIG. 5A), which is attached to the vacuum chamber and configured to translationally displace the nozzle shaft inwardly and outwardly of the vacuum chamber. A stationary support bracket 104 (best seen in FIG. 5A) is provided within the vacuum chamber 34 for slidably supporting the nozzle shaft 102 at the end thereof on the side of the post 100 away from the stepping motor 103. The support bracket 104 also prevents inward movement of the nozzle shaft 102 as the post 100 is inwardly displaced and comes in contact with the bracket. Thus, the support bracket 104 additionally serves as an inward translational boundary of the nozzle shaft 102.

A paddle 105 (best seen in FIGS. 5A and 5C) is attached to the nozzle shaft 102 at the end near the stepping motor 103. It has a horizontal section 106 that is attached to, and extends along, a portion of the length of the nozzle shaft 102, and a vertical section 107 that extends downwardly generally at a right angle from the end of the horizontal section near the stepping motor 103. When the nozzle shaft 102 is outwardly displaced from the vacuum chamber 34 by the stepping motor 103, the vertical section 107 comes in contact with a microswitch 108, which energizes to stop the stepping motor operation. The vertical section 107 and the microswitch 108 thus define the outward translational boundary of the nozzle shaft 102.

Also attached to the outside of the vacuum chamber 34 is a stepping motor 109 including a push arm 110 (best seen in FIGS. 5A and 5C). When energized, the stepping motor 109 is adapted to push up against the horizontal section 106 via the push arm 110. In this manner, the nozzle shaft 102 is made to axially rotate in a forward direction. The rotation of the nozzle shaft 102 in a reverse direction is effectuated by a spring 111 (best seen in FIG. 5C) which is attached above the stepping motor 109 and presses down on the horizontal section 106. Thus, when the stepping motor 109 is deenergized, the paddle 105 is pushed downwardly by the spring 111 which forces the nozzle shaft 102 to rotate in the reverse direction until the horizontal section 106 rest on top of a microswitch 112 (best seen in FIG. 5C). The forward rotation of the nozzle shaft 102 by the stepping motor 109 is limited by a micrometer 113. Attached above the stepping motor 109, the micrometer 113 is adjusted so that the horizontal section 106 of the paddle 105 contacts the micrometer after a predetermined range of forward rotation. As in the operation of the stepping motor for controlling the axial rotation of the sample disk 40, the operation of both of the stepping motors 103, 109 are controlled by the computer (not shown).

As the nozzle shaft 102 axially rotates and is displaced in the above-described fashion, the delivery nozzle 42, which is attached to the nozzle shaft via the post 100, is correspondingly radially pivoted and horizontally displaced relative to the sample disk 40, respectively (best seen in FIGS 5A and 6 illustrated by a phantom outline 42A). This arrangement allows the delivery nozzle 42 to be positioned completely away from the mirrored surface 30 to prevent the deposition of excess sample on, or to dump unwanted solvent away from, the mirrored surface. It is important to note that the displacement of the delivery nozzle 42 by the stepping motors 103, 109 is permitted by the flexibility of the transfer tube 91, which is achieved by the relatively long length per diameter of the tube and the chosen material. This feature is not contemplated by prior art sampling devices of this type.

During the sample deposition, the delivery nozzle 42 is placed in a deposit position, where the delivery nozzle is positioned horizontally within the width of, and approximately 0.010 inch radially away from, the mirrored surface 30 (best seen in FIGS. 5A and 6). The distance between the delivery nozzle 42 and the mirrored surface 30 during the sample deposition is maintained by the micrometer 113 which is adjusted to halt the rotation of the nozzle shaft 102 by the stepping motor 109 in the method described above when the delivery nozzle 42 is a prescribed distance away from the mirrored surface 30, which is 0.010 inch in the preferred embodiment. In this manner, the delivery nozzle 42 is prevented from coming in contact with, and possibly scratching the mirrored surface 30.

When the sample is not being deposited upon the mirrored surface 30, the delivery nozzle 42 is placed in a rest position, as illustrated by the phantom outline 42A (best seen in FIGS 5A and 6), where the delivery nozzle 42 is radially pivoted away from the deposit position and displaced horizontally beyond the width of the heat shield 31. The pivoting away of the delivery nozzle 42 is accomplished by the spring 111 as it presses down on the horizontal section 106 of the paddle 105 to cause the nozzle shaft 102 to rotate in the reverse direction that would correspondingly pivot the delivery nozzle 42 away from the mirrored surface 30. The rotation of the nozzle shaft 102 in this direction is allowed because the stepping motor 109 is deenergized when the sample is not being deposited. The horizontal displacement of the delivery nozzle 42 is achieved by the inward displacement of the nozzle shaft 102 by the stepping motor 103.

Figure 8:
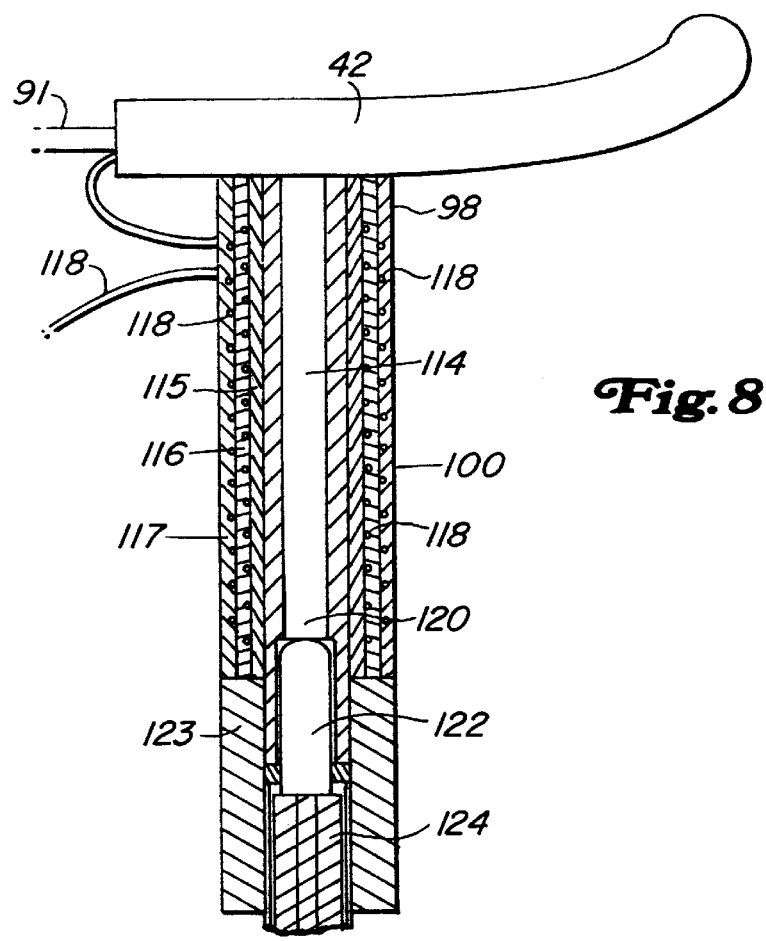
FIG. 8 is a sectional view of a nozzle post taken along line 8—8 of FIG. 6 and in the direction generally indicated.

Referring now to FIG. 8, in accordance with another important aspect of the present invention, the post 100 includes a copper core 114, which is coated with three layers 115, 116, 117 of high temperature cement. Wrapped around the core 114 and embedded within the second layer 116 and the third layer 117 is a nichrome wire 118. Also included in the post 100, and cemented to a bottom end 120 of the core 114, is a RTD temperature probe 122. A machinable glass ceramic spool 123 is used to secure the copper core 114 and the temperature probe 122 to a stainless steel tube 124, with a high temperature cement being used as an adhesive between these components.

When electric current of about 1.2A is applied to the wire 118, the post 100 effectively acts as a heater to eliminate a cold spot at the point on the delivery nozzle 42 that is connected to the post 100. To facilitate heat transfer, the delivery nozzle 42 is made of copper. The current applied to the wire 118 also conducts through the transfer tube 91 resulting in the temperatures within the transfer tube and the deliver nozzle 42 to be about equal. The preferred temperature should be approximately 250° to 300° C. to effectively prevent condensing of the sample before it is deposited onto the mirrored surface 30.

Referring back to FIG. 1, the path followed by the IR beam 32 is shown. The IR beam 32 is generated by the IR spectrometer 24 and directed onto a steering mirror 126, which redirects the IR beam 32 onto a first directing mirror 128 through the inlet window 36. Reflecting from the first directing mirror 128, the IR beam 32 is directed onto the focusing objective mirror 84, which focuses the IR beam 32 onto the examination point 82 (best seen in FIG. 6) of the mirrored surface 30. After being reflected from the examination point 82, the IR beam 32 is received by the defocusing objective mirror 86, which deflects the IR beam 32 onto a second directing mirror 130. Then, the IR beam 32 is directed by the second directing mirror 130 to exit the vacuum chamber 34 through the outlet window 38. A detector mirror 132 receives the IR beam 32 passing through the outlet window 38 and focuses it onto the IR detector 26 to be recorded and analyzed in a known manner by the computer (not shown).

Figure 9:
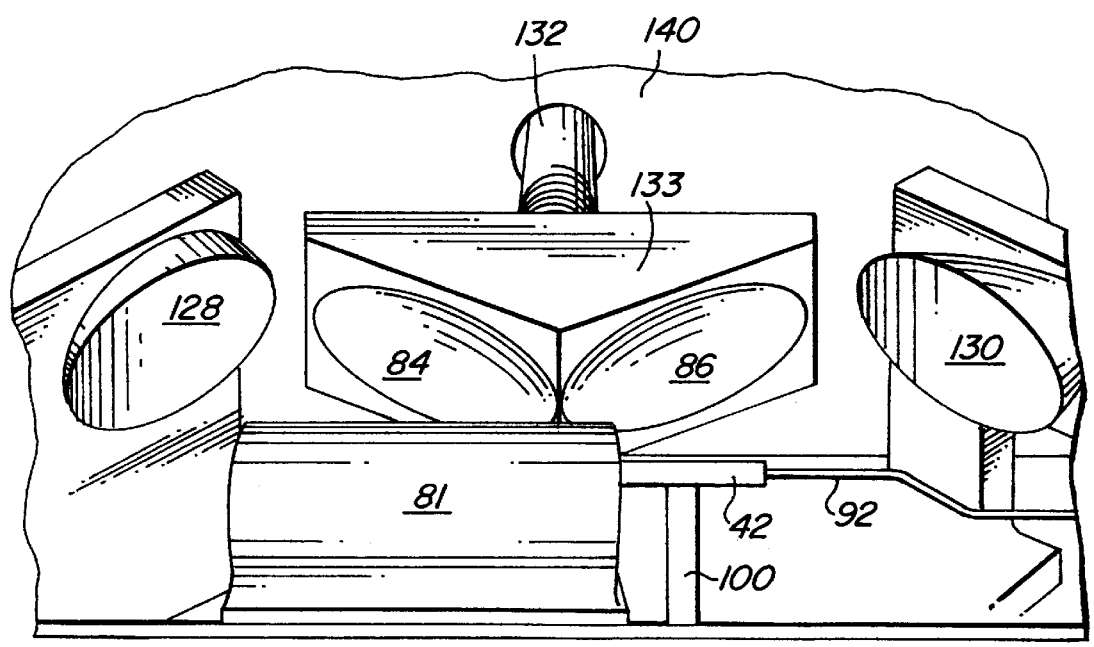
FIG. 9 is a top perspective view of objective mirrors that are a part of the present invention.

Referring now to FIG. 9, the focusing and the defocusing objective mirrors 84, 86 are shown viewed from inside the chamber 34 and behind the heat shield 81. Each objective mirror 84, 86 has a generally parabolic shape, and is intrinsically aligned relative to each other by being single point diamond turned from a single block of aluminum 133. Each of the objective mirrors 84, 86 is coated with gold to provide a smooth reflecting surface. Through the fabricating process, the foci of the two objective mirrors 84, 86 are set to be coincident, i.e., the focal points of the light reflecting from these mirrors are the same. With this configuration, there is no need to adjust the objective mirrors 84, 86 relative to each other to coincide the foci.

Figure 10:
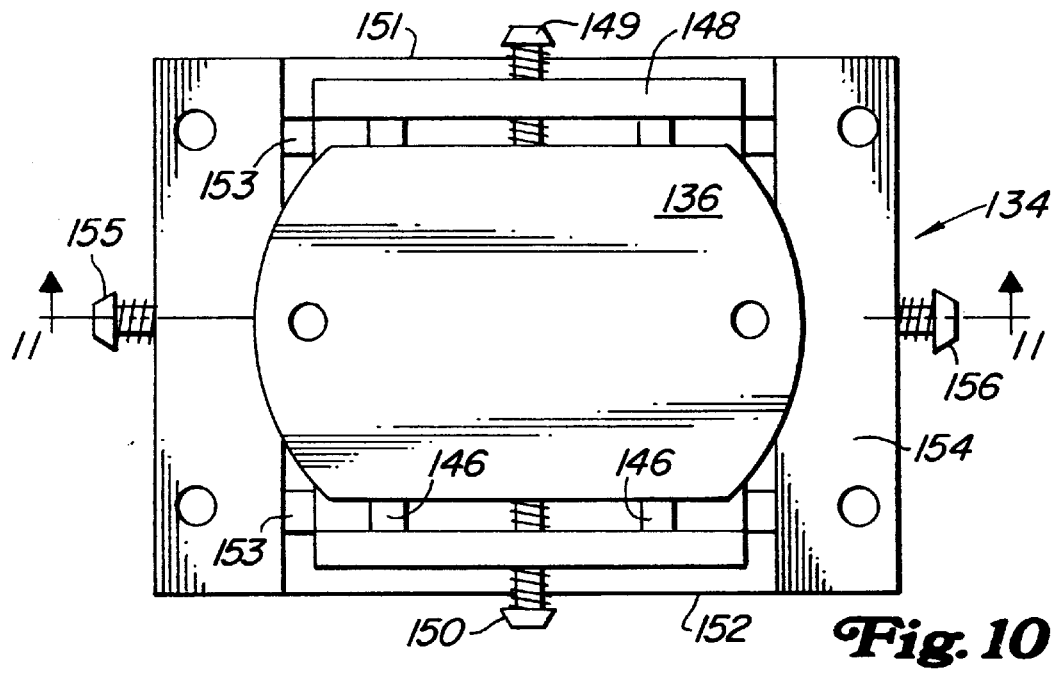
FIG. 10 is a front elevational view of a mirror positioner that is used to adjust the mirrors of FIG. 9.
Figure 11:
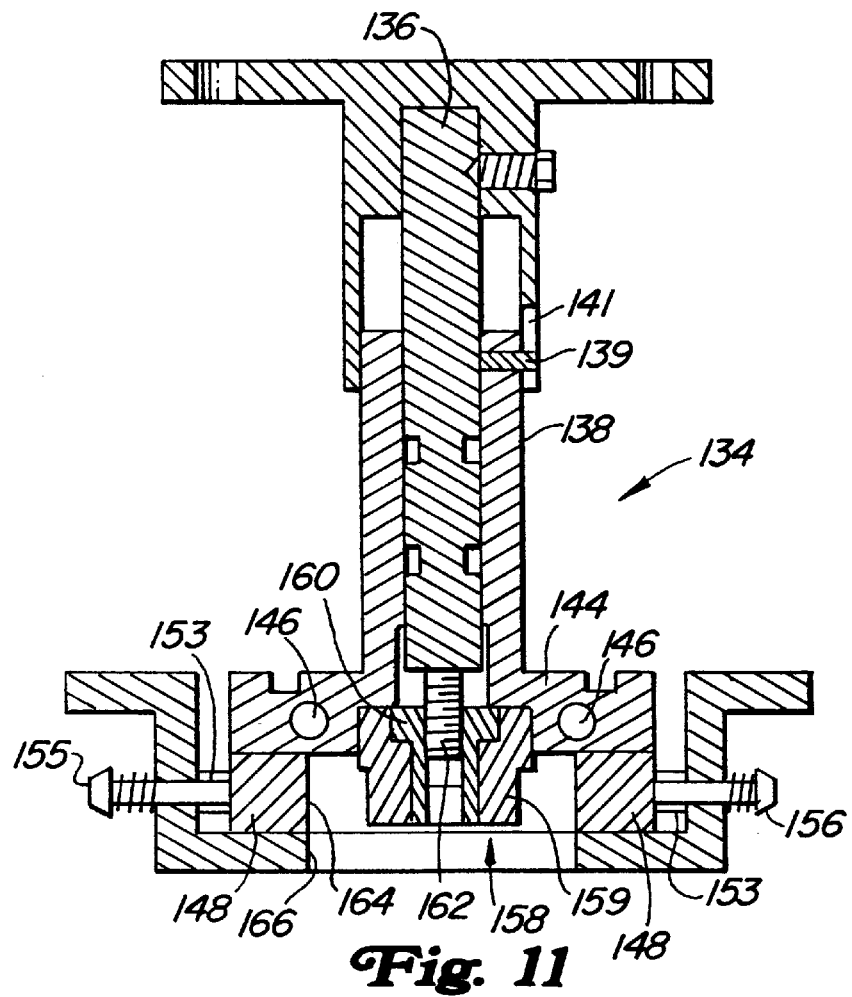
FIG. 11 is a sectional view of the mirror positioner taken along line 11—11 of FIG. 10 and in the direction generally indicated.

Referring now to FIGS. 10 and 11, a mirror positioner is shown and generally designated 134. Included in the mirror positioner 134 is a position piston 136 which is connected to the aluminum block 133 (best seen in FIG. 9) on the side opposite the objective mirrors 84, 86 for supporting the objective mirrors 84, 86. The position piston 136 is slidably received by a cylindrical position probe 138. The position probe 138 has a fixed pin 139 which protrudes therefrom and is inserted into a longitudinal slot 141 to allow the position piston 136 to be longitudinally displaced while preventing any rotational movement. Penetrating through a wall 140 of the vacuum chamber 34, which is opposite a wall 142 having the inlet and the outlet windows 36, 38 (best seen in FIG. 1), the position probe 138 has a generally square base 144 that is slidably attached to a pair of spaced parallel, vertical rails 146 fixed on a generally rectangular glider 148. The vertical length of the glider 148 is longer than that of the base 144 so that the base is allowed to slide up and down on the rails 146, i.e., along the Y-axis. Adjustment of screws 149, 150 at the top 151 and at the bottom 152 of the glider 148, respectively, (best seen in FIG. 10) secures the position probe 138 to a desired position along the rails 146.

The glider 148, similar to the base 144, is slidably attached to a pair of spaced parallel horizontal rails 153 fixed on a generally rectangular bridge 154. The horizontal length of the bridge 154 is longer than that of the glider 148 so that the glider, including the probe 138, is allowed to slide horizontally along the rails 153, i.e., along the X-axis. Screws 155, 156 hold the glider 148 to a desired position along the rails 153 as they are adjusted to displace the glider.

The displacement of the position piston 136 within the position probe 138 is performed by a piston driver generally designated 158 and includes an externally threaded outer nut 159 and an internally threaded inner nut 160. Screwed into the base 144, the outer nut 159 prevents the inner nut 160 from being displaced translationally, but permits it to be axially rotated. Thus arranged, the inner nut 160 is adapted to receive a threaded stem 162 connected to the end of the position piston 136 opposite from the aluminum block 133 (best seen in FIG. 9). The piston driver 158 is located within holes 164, 166 in the glider 148 and bridge 152, respectively (best seen in FIG. 11). When the inner nut 160 is axially rotated, the position piston 136 is correspondingly driven inwardly or outwardly of the position probe 138, i.e., along the Z-axis, without any axial rotation.

Configured as described above, the mirror positioner 134 controls the adjustment of the objective mirrors 84, 86, which are attached to the end of the position piston 136, in three dimensions, i.e., in the X, Y and Z directions. In this manner, the foci of the objective mirrors 84, 86 can be positioned precisely on the examination point 82 while preserving the real time analysis feature of the present system, since the location of the mirrors 84, 86 enables the examination point 82 to be in close proximity to the sample disposition points.

It will be appreciated that one important advantage of the present sample analysis system is that the rotation of the sample disk 40 is not dependent upon the cooling device 72. This significantly simplifies the system manufacturing process, and allows for a more precise displacement of the sample disk 40. Another major advantage of the present invention is that the delivery nozzle 42 can be positioned to prevent excess samples and unwanted solvent from contaminating the disk 40. Another significant advantage is that the two objective mirrors 84, 86 are formed from a single block 136, which eliminates the need to adjust the mirrors relative to each other. Still another advantage of the present invention apparatus is that the block 136 is also adjustable in three dimensions, i.e., along the X, Y and Z axes, which allows for a more precise focusing of the infrared beam upon the examination point 82. Yet another advantage of the present invention is that the sample deposition point 88 is at close proximity to the examination point 82 to enable "real time" examination of the sample.

While a particular embodiment of the matrix isolation apparatus for spectroscopic analysis of chemical compounds of the invention has been shown and described, it will be appreciated by those skilled in the art that changes and modification may be made thereto without departing from the invention in its broader aspects and as set forth in the following claims.

I claim:

1. Apparatus for spectroscopic analysis of chemical compounds in samples released from a gas chromatograph, said apparatus configured for placing the samples in matrix isolation for exposure to a beam of light generated from a spectrometer, and comprising:
    a vacuum chamber;
    a generally cylindrical, axially rotating sample disk housed within said vacuum chamber and having a mirrored surface and an axle, said mirrored surface configured for receiving the samples from the gas chromatograph;
    support means for supporting said rotating disk within said vacuum chamber; and
    cooling means for cooling said mirrored surface to cryogenic temperatures;
    said support means being mounted on said cooling means and adapted to conduct heat transfer between said cooling means and said mirrored surface of said sample disk so that said mirrored surface is cooled to said cryogenic temperatures and, said disk being configured to rotate relative to said support means and said cooling means, which are stationary.

2. The apparatus as defined in claim 1 wherein said disk simultaneously rotates and moves translationally along its axis relative to said stationary cooling means to define a helical pattern.

3. The apparatus as defined in claim 2 including a spur gear secured to said disk, said spur gear being concentric with and axially offset from said disk, a driven pinion gear engaged with said spur gear for rotating said disk, and said axle having a threaded region engaged with a thrust nut fixed to said support means for moving said disk translationally along its axis.

4. The apparatus as defined in claim 2 wherein said support means include a spring loaded split bearing configured to accommodate said axle for translational and rotational movement to permit said disk to rotate in said helical pattern.

5. The apparatus as defined in claim 4 wherein said split bearing is made of silver for providing lubricity at low temperatures.

6. The apparatus as defined in claim 1 further including deposition means for depositing the samples on said mirrored surface, said deposition means being configured to be displaceable between a deposit position and a rest position.

7. The apparatus as defined in claim 6 wherein said deposition means includes a flexible transfer tube disposed at least partially in said vacuum chamber and having a delivery nozzle for depositing the samples onto said mirrored surface.

8. The apparatus as defined in claim 7 wherein said transfer tube is a metal tube resistance heated by an electric current that flows along its length.

9. The apparatus as defined in claim 7 wherein said transfer tube is fitted internally with a used silica tube to provide an inert surface for the transmission of the samples therethrough.

10. The apparatus as defined in claim 7 wherein said transfer tube is fitted internally with a stainless steel tube with a silica lining to provide an inert surface for the transmission of the samples therethrough.

11. The apparatus as defined in claim 7 wherein a portion of said transfer tube outside said vacuum chamber is encased within a vacuum extension tube being in fluid communication with said vacuum chamber.

12. The apparatus as defined in claim 7 further including displacing means connected to said delivery nozzle for movably displacing said delivery nozzle in at least one of a radial and a horizontal direction relative to said mirrored surface.

13. The apparatus as defined in claim 12 wherein said displacing means include a post connected to said delivery nozzle, two digital stepping motors located externally of said vacuum chamber, and a shaft having a first end connected to said post and a second end connected to one of said two stepping motors, said two stepping motors configured to perform at least one of rotating and axially displacing said shaft.

14. The apparatus as defined in claim 13 wherein said post is heated to generally correspond to the temperature of said delivery nozzle.

15. The apparatus as defined in claim 1 further including focusing means for focusing the beam entering through an inlet window in said vacuum chamber onto an examination point on said mirrored surface for penetration through the sample; and
    position control means located externally of said vacuum chamber and connected to said focusing means for controlling the position of said focusing means.

16. The apparatus as defined in claim 15 wherein said focusing means includes two objective mirrors formed on a single block.

17. The apparatus as defined in claim 16 further including a pair of directing mirrors for directing the beam entering through said inlet window onto one of said two objective mirrors and for receiving the beam reflected from the other of said two objective mirrors.

18. The apparatus as defined in claim 16 wherein said objective mirrors are coated with gold.

19. The apparatus as defined in claim 15 wherein said position control means adjust the position of said focusing means in X, Y and Z directions.

20. The apparatus as defined in claim 1 further including deposition means for depositing the samples on said mirrored surface and focusing means for focusing the beam onto an examination point on said mirrored surface for penetration through the sample, the samples being deposited on said mirrored surface at a close proximity to and upstream of said examination point to enable real time examination of the samples.

21. The apparatus as defined in claim 20 wherein said focusing means includes a first objective mirror for focusing the beam onto said examination point and a second objective mirror for receiving the beam reflected from said examination point, the beam focused onto and received from said examination point defining a generally horizontal plane, and said sample disk rotates in a direction that is perpendicular to said plane to enable said real time examination.

22. Apparatus for spectroscopic analysis of chemical compounds in samples released from a gas chromatograph, said apparatus configured for placing the samples in matrix isolation for exposure to a beam of light generated from a spectrometer, and comprising:

a vacuum chamber having an inlet window for allowing the beam of light to enter said vacuum chamber and an outlet window for allowing the beam to exit said vacuum chamber;

a generally cylindrical, axially rotating sample disk housed within said vacuum chamber and having a mirrored surface, said mirrored surface configured for receiving the samples from the gas chromatograph;

focusing means for focusing the beam entering through said inlet window onto an examination point on said mirrored surface for penetration through the sample, and for receiving the beam reflected from said examination point;

position control means located externally of said vacuum chamber and connected to said focusing means for controlling the position of said focusing means in X, Y and Z directions; and detecting means disposed relative to said mirror means for detecting the beam received by said mirror means from said examination point.

23. The apparatus as defined in claim 22 wherein said focusing means includes two objective mirrors formed on a single block.

24. The apparatus as defined in claim 23 further including a pair of directing mirrors for directing the beam entering through said inlet window onto one of said two objective mirrors, and for receiving the beam reflected from the other of said two objective mirrors and directing the received beam out of said vacuum chamber through said outlet window.

25. The apparatus as defined in claim 24 wherein said detecting means detects the beam directed out of said outlet window.

26. Apparatus for spectroscopic analysis of chemical compounds in samples released from a gas chromatograph, said apparatus configured for placing the samples in matrix isolation for exposure to a beam of light generated from a spectrometer and comprising:

a vacuum chamber;

a generally cylindrical, axially rotating sample disk housed within said vacuum chamber and having a mirrored surface, said mirrored surface for receiving the samples from the gas chromatograph;

deposition means for depositing the sample on said mirrored surface, said deposition means including a flexible transfer tube disposed at least partially in said vacuum chamber and having a delivery nozzle for depositing the samples onto said mirrored surface; and displacing means connected to said deposition means for pivotally and transversely displacing said deposition means between a deposit position and a rest position.

27. The apparatus as defined in claim 26 wherein said transfer tube is a metal tube resistance heated by an electric current that flows along its length.

28. The apparatus as defined in claim 26 wherein said transfer tube is fitted internally with a fused silica tube to provide an inert surface for the transmission of the samples therethrough.

29. The apparatus as defined in claim 26 wherein said transfer tube is fitted internally with a stainless steel tube with a silica lining to provide an inert surface for the transmission of the samples therethrough.

30. The apparatus as defied in claim 26 wherein a portion of said transfer tube outside said vacuum chamber is encased within a vacuum extension tube being in fluid communication with said vacuum chamber.

31. The apparatus as defined in claim 26 wherein said displacing means displace said deposition means in at least one of a radial and a horizontal direction relative to said mirrored surface.

32. The apparatus as defined in claim 26 wherein said displacing means include a post connected to said deposition means, two digital stepping motors located externally of said vacuum chamber, and a shaft having a first end connected to said post and a second end connected to one of said two stepping motors, said two stepping motors configured to perform at least one of rotating and axially displacing said shaft.

33. The apparatus as defined in claim 32 wherein said post is heated to generally correspond to the temperature of said delivery nozzle.

34. Apparatus for spectroscopic analysis of chemical compounds in samples released from a gas chromatograph, said apparatus configured for placing the samples in matrix isolation for exposure to a beam of light generated from a spectrometer and comprising:

a vacuum chamber;

a generally cylindrical, axially rotating sample disk housed within said vacuum chamber and having a mirrored surface, said mirrored surface for receiving the samples from the gas chromatograph; and deposition means for depositing the sample on said mirrored surface, the samples being deposited on said mirrored surface at less than 90° upstream of an examination point to enable real time examination of the samples.

35. The apparatus as defined in claim 34 further including focusing means for focusing the beam onto said examination point on said mirrored surface for penetration through the sample, the beam defining a generally horizontal plane, and wherein said sample disk rotates in a direction that is perpendicular to said plane to enable said real time examination of the samples.

* * * * *